United States Patent [19]

Watts, Jr. et al.

[11] 4,367,352

[45] Jan. 4, 1983

[54] OLIGOMERIZED OLEFINS FOR LUBRICANT STOCK

[75] Inventors: Lewis W. Watts, Jr.; Edward T. Marquis, both of Austin, Tex.

[73] Assignee: Texaco Inc., White Plains, N.Y.

[21] Appl. No.: 219,119

[22] Filed: Dec. 22, 1980

[51] Int. Cl.$^3$ .................................................. C07C 2/74
[52] U.S. Cl. ..................................... 585/254; 585/255; 585/515; 585/522; 585/526; 585/643
[58] Field of Search ............... 585/254, 255, 515, 526, 585/643, 522

[56] References Cited

U.S. PATENT DOCUMENTS

| | | | |
|---|---|---|---|
| 3,149,178 | 9/1964 | Hamilton et al. | 585/255 |
| 3,742,082 | 6/1973 | Brennan | 585/255 |
| 4,038,213 | 7/1977 | McClure | 252/430 |
| 4,065,512 | 12/1977 | Cares | 585/508 |
| 4,218,330 | 8/1980 | Shubkin | 252/46.6 |

OTHER PUBLICATIONS

"Research Disclosure" Industrial Opportunities Ltd., Section 19515, pp. 270-271, Jul. 1980.

*Primary Examiner*—Curtis R. Davis
*Attorney, Agent, or Firm*—Jack H. Park; Kenneth R. Priem; David L. Mossman

[57] ABSTRACT

A process is disclosed for the production of high quality synthetic lubricants which comprises transforming ethylene into a mix of alpha olefins, separating from this mix of alpha olefins the alpha olefins in the range from about 14 to 20 carbon atoms, oligomerizing the alpha olefins in the range from about 14 to 20 atoms with a perfluorosulfonic acid resin catalyst and hydrogenating these oligomerized olefins. The olefins from the original mix of alpha olefins which are lighter and heavier than the 14 to 20 carbon atom alpha olefins processed above are combined and subjected to an isomerization/disproportionation process and the resulting olefins in the range of about 14 to 20 carbon atoms are oligomerized with perfluorosulfonic acid resin catalyst as above. Optionally, these olefins in the range of 14 to 20 carbon atoms may be combined with the olefins prepared directly from ethylene before oligomerization takes place. The resulting oligomers are hydrogenated. The olefins from the isomerization/disproportionation process which are less than 14 carbon atoms or greater than 20 carbon atoms are once again subjected to the isomerization/disproportionation process as above, the 14 to 20 carbon atom cut is oligomerized, and the process is repeated. The resulting hydrogenated oligomerized olefins are useful in internal combustion engines as crankcase lubricants.

8 Claims, No Drawings

OLIGOMERIZED OLEFINS FOR LUBRICANT STOCK

BACKGROUND OF THE INVENTION

1. Field of the Invention

This invention pertains to the field of synthetic lubricants.

2. Description of the Prior Art

The prior art contains teachings of oligomerization of alpha olefins. These prior art processes use Friedel-Crafts catalysts and are exemplified by U.S. Pat. No. 4,218,330 which discloses dimerizing C-12 to C-18 alpha olefins; U.S. Pat. No. 3,742,082 which discloses dimerizing C-6 to C-10 alpha olefins; and U.S. Pat. No. 3,149,178 which discloses oligomerizing C-6 to C-12 alpha olefins. The use of Friedel-Crafts catalysts such as boron trifluoride or aluminum chloride requires washing after oligomerization to remove catalyst and subsequent drying.

U.S. Pat. No. 4,065,512 discloses the use of perfluorosulfonic acid resin membranes to catalyze the hydration and/or polymerization of isobutene. U.S. Pat. No. 4,038,213 concerns alkylation of isoparaffins by addition of an olefin and other reactions using a supported solid perfluorinated polymer of like chemical composition to that used in U.S. Pat. No. 4,065,512. U.S. Pat. No. 4,038,213 discloses that olefins of from C-2 to C-5 will polymerize if the isoparaffin is not used in large excess.

SUMMARY OF THE INVENTION

The invention is the production of high guality synthetic lubricants which comprises transforming ethylene into a mix of alpha olefins, separating from this mix alpha olefins in the range from about 14 to 20 carbon atoms, oligomerizing the alpha olefins in the range from about 14 to to 20 atoms with a perfluorosulfonic acid resin catalyst and hydrogenating these oligomerized olefins. The olefins from the original mix of alpha olefins which are lighter and heavier than the 14 to 20 carbon atom alpha olefins processed above are combined and subjected to an isomerization/disproportionation process and the resulting olefins in the range of about 14 to 20 carbon atoms are oligomerized with perfluorosulfonic acid resin catalyst as above. Optionally, these olefins in the range of 14 to 20 carbon atoms may be combined with the olefins prepared directly from ethylene before oligomerization takes place. The resulting oligomers are hydrogenated. The olefins from the isomerization/disproportionation process which are less than 14 carbon atoms or greater than 20 carbon atoms are once again subjected to the isomerization/disproportionation process as above, the 14 to 20 carbon atom cut is oligomerized, and the process is repeated. The resulting hydrogenated oligomerized olefins are useful in internal combustion engines as crankcase lubricants.

DESCRIPTION OF THE PREFERRED EMBODIMENTS

The perfluorosulfonic acid resins are copolymers of sulfonyl fluorovinyl ether and a fluorocarbon and may have the following formula:

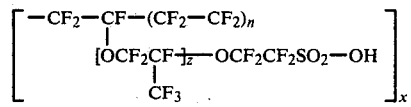

where X represents repeating units. Actually the so called XR resin (the sulfonyl fluoride form) is produced first and made into film. Then the fluoride film is hydrolyzed to the sodium sulfonate, which is finally converted to the acid form.

The formula weight corresponding to one sulfonyl acid group is called the equivalent weight. The properties of the resin depend on the equivalent weight; the higher the equivalent weight, the higher is the mechanical strength, but also the higher is the electrical resistance. Perfluorosulfonic acid resin with useful properties has an equivalent weight ranging from 1,100 to 1,500, corresponding to $z=1$, and $n=15$ to 20.

The commercial resin is available as a membrane 5 to 10 mils thick and is sometimes laminated with a polytetrafluoroethylene web to improve mechanical strength and dimensional stability. The resin is also available in pellet and powder form. The physical form of the resin is a matter of choice for one skilled in the art. All forms will provide the catalytic effect of this invention. Engineering considerations will determine the most suitable physical form.

A further description of the perfluorosulfonic acid resin is given in duPont "Innovation", Volume 4, No. 3, Spring, 1973 and in U.S. Pat. No. 4,038,213 and patents filed therein which are incorporated herein by reference.

The olefins to be oligomerized in this invention are obtained by a multi-step process. In the first step, ethylene is tranformed into linear alpha olefins using Ziegler technology as disclosed in various patents, including U.S. Pat. Nos. 3,424,815; 3,482,000; 3,424,816; 3,444,264; 3,444,263; 3,502,741; 3,510,539; 3,478,124; and 3,441,631. These patents are incorporated herein by reference. The result of this conversion of ethylene is a mixture of alpha olefins ranging from C-4 to above C-20. The alpha olefins ranging from about C-14 to C-20 or any other range of alpha olefins desired within C-14 to C-20 are separated and oligomerized using the perfluorosulfonic acid resin catalyst described above. The alpha olefins of below about 14 and above about 20 carbon atoms are combined and subjected to an isomerization/disproportionation process described in the literature, for example: U.S. Pat. Nos. 3,647,906; 3,728,414 and 3,726,938, which are incorporated herein by reference.

The olefins resulting from this isomerization/disproportionation process are a mixture of alpha and internal olefins of various molecular weights. The olefins in the range from about 14 to 20 carbon atoms or any selected cut within that range may be oligomerized with the perfluorosulfonic acid resin as above. Optionally, those olefins may be mixed with the alpha olefins from the initial ethylene made feed and oligomerized. The olefins lying outside the range to be oligomerized are combined and subjected to the isomerization/disproportionation process again. This process can be carried on indefinitely.

Such a process provides a systematic way to control which olefin cut is selected for oligomerization, and also uses the discarded cuts for additional feed.

We have discovered that the perfluorosulfonic acid resins in the acid form are very selective catalysts for the formation of lower oligomers of alpha olefins. Olefins as described above contacted with the perfluorosulfonic acid resins described above oligomerize in a highly selected manner to dimer, trimer, tetramer, and vanishing amounts of pentamer. The oligomerization occurs both in the batch treatment and the continuous treatment. The batch or continuous treatment yields oligomers which usually contain high ratios of dimer to trimer and high ratios of trimer to tetramer.

The oligomerization occurs neat (to solvent needed) and at temperatures from 60° to 250° C., preferably from about 100° to 200° C. Depending on which olefin is used, there is a threshold temperature at which oligomerization will proceed. Below the threshold temperature little or no reaction occurs. The reaction can proceed at autogenous pressures. However, if superatmospheric pressures are found to be advantageous, they are also acceptable. In a continuous process, the LHSV may vary over a wide range. However, the LHSV is recommended to range from about 1/16 to 2. One skilled in the art can adjust the LHSV to suit the particular situation.

The method of our invention makes valuable lower oligomers selectively using a solid fixed bed catalyst requiring no hydrolysis or washing to remove the catalyst, as is the case with boron trifluoride and/or aluminum trichloride. It is surprising that such high dimer to trimer selectivity occurs at good conversions, yet the reaction terminates before high molecular weight species are formed in appreciable quantities.

In order to form materials which have adequate oxidative stability for lubricants, the oligomerized olefins are optionally hydrogenated either partially or totally. This hydrogenation is done by procedures known to those skilled in the art as exemplified by U.S. Pat. Nos. 4,045,508; 4,013,736; 3,997,622 and 3,997,621. A particularly preferred catalyst for this hydrogenation is a nickel, copper, chromia catalyst described in U.S. Pat. No. 3,152,998 and is referred to in this application as Ni-2715.

The following examples will illustrate the invention but are not intended to be limiting.

EXAMPLE I

To a 1000 ml RB flask fitted with mechanical stirrer, condenser, $N_2$ inlet and bubbler, and thermometer were added 500 grams of Shell's C-13/C-14 mixed internal olefins[1] 53.4% C-13, 45.0% C-14, 0.5% C-15, and 1.1% hydrocarbon) and 5.0 grams of NAFION 501[2] ion exchange resin catalyst in the $H^+$ form. The reaction mixture was heated at 150° C. with stirring for 19¾ hours. The catalyst was removed by filtration. Gel permeation chromatography indicated conversion to C-26 and higher carbon oligomers was approximately 83.6% (C-13/C-14≅16.4%, C-26/27/28≅69.1%, C-39/40/41/42≅14.5%).

[1]Similar olefin mixtures are obtained by the isomerization/disproportionation process disclosed heretofore.
[2]NAFION 501 is a powdered form of perfluorosulfonic acid resin. All examples use the acid form of the resin. Product of E. I. duPont de Nemours & Co.

EXAMPLE II

To a 1-liter stainless steel autoclave was added 300.0 grams of oligomer made in ExampleI and 15.0 grams of Ni-2715 catalyst in powdered form. The reaction mixture was stirred at 210° C. in the presence of 2000 psig hydrogen pressure for four hours. The catalyst was removed by filtration and the clear, nearly water-white fluid had the following desirable properties after removal of monomer under high vacuum stripping to a pot temperature of 180° C.

| | | |
|---|---|---|
| Viscosity, 210° F., cst | = | 3.93 |
| VI | = | 92.3 |
| Pour point | = | < −50° F. |

Three hydrogenations were completed on three different oligomers from Shell's C-13/C-14 internal olefin mixture and the hydrogenated synlube fluids after removal of monomer had 210° F. viscosities in the range of 3.9–4.5 cst at 210° F., viscosity indices in the 90–95 range and pour points which ranged from −40° F. to < −50° F. Volatilities were also good, with 93–95% sample remaining at 194° C. and 74–78% remaining at 233° C.

We claim:
1. A process for the production of high quality synthetic lubricants which comprises
   a. transforming ethylene into a mixture of alpha olefins,
   b. separating from the mixture of (a) the alpha olefins in the range from about 14 to 20 carbon atoms,
   c. oligomerizing the alpha olefins of from about 14 to 20 carbon atoms from (b) with a perfluorosulfonic acid resin catalyst at a temperature sufficient to effect oligomerization,
   d. combining the olefins from step (b) which are outside the range of from about 14 to 20 carbon atoms,
   e. subjecting the olefins from (d) to an isomerization/disproportionation process to provide a mixture of olfins,
   f. separating from the mixture the olefins made in (c) those olefins in the range of from about 14 to 20 carbon atoms,
   g. oligomerizing the olefins of from about 14 to 20 carbon atoms from (f) with a perfluorosulfonic acid resin catalyst at a temperature sufficient to effect oligomerization,
   h. combining the olefins from (f) which are outside the range of from about 14 to 20 carbon atoms,
   i. subjecting the olfins from (h) to an isomerization/disproporationation process to provide a mixture of olefins,
   j. repeating steps (f) through (i) and,
   k. hydrogenating the oligomers from steps (c) and (g)
2. A process as in claim 1 wherein the temperature in step (c) ranges from about 60 to 250° C.
3. A process as in claim 2 wherein the temperature ranges from about 100° to 200° C.
4. A process as in claim 1 wherein the pressure is autogenous.
5. A process for the production of high quality synthetic lubricants which comprises
   a. transforming ethylene into a mixture of alpha olefins,
   b. separating from the mixture of (a) the alpha olefins in the range from about 14 to 20 carbon atoms,
   c. oligomerizing the alpha olefins of from about 14 to 20 carbon atoms from (b) with a perfluorosulfonic acid resin catalyst at a temperature sufficient to effect oligomerization,
   d. combining the olefins from step (b) which are outside the range of from about 14 to 20 carbon atoms, e. subjecting the olefins from (d) to an isomerization/disproportionation process to provide a mixture of olefins, f. separating from the mixture the olefins made in (c) those olefins in the range of from about 14 to 20 carbon atoms, g. oligomerizing the olefins of from about 14 to 20 carbon atoms from (f) with a perfluorosulfonic acid resin catalyst at a temperature sufficient to effect oligomerization, h. combining the olefins from (f) which are outside the range of from about 14 to 20 carbon atoms, i. subjecting the olefins from (h) to an isomerization/disproportionation process to provide a mixture of olefins, j. repeating steps (f) through (i).

6. A process as in claim 5 wherein the temperature in step (c) ranges from about 60° to 250° C.

7. A process as in claim 6 wherein the temperature ranges from about 100° to 200° C.

8. A process as in claim 5 wherein the pressure is autogenous.

* * * * *